United States Patent [19]

Kiener et al.

[11] Patent Number: 5,516,661

[45] Date of Patent: May 14, 1996

[54] MICROBIOLOGICAL PROCESS FOR THE PRODUCTION OF AROMATIC HYDROXY-HETEROCYCLIC CARBOXYLIC ACIDS

[75] Inventors: Andreas Kiener, Visp; Markus Rohner, Glis; Klaus Heinzmann, Visperterminen, all of Switzerland

[73] Assignee: Lonza Ltd., Gampel/Valais, Switzerland

[21] Appl. No.: 384,695

[22] Filed: Feb. 3, 1995

Related U.S. Application Data

[63] Continuation of Ser. No. 984,450, Dec. 2, 1992, abandoned.

[30] Foreign Application Priority Data

Dec. 5, 1991 [CH] Switzerland ............................. 3572/91

[51] Int. Cl.[6] ............................. C12P 17/12; C12N 1/20
[52] U.S. Cl. ................. 435/122; 435/252.1; 435/253.3; 435/822; 435/829; 435/874
[58] Field of Search ..................................... 435/122, 146, 435/252.1, 253.3, 822, 829, 874

[56] References Cited

U.S. PATENT DOCUMENTS

| | | | |
|---|---|---|---|
| 4,738,924 | 4/1988 | Kulla et al. | 435/121 |
| 5,151,351 | 9/1992 | Hoeks | 435/824 |
| 5,273,893 | 12/1993 | Kiener | 435/122 |

FOREIGN PATENT DOCUMENTS

| | | |
|---|---|---|
| 152948 | 4/1985 | European Pat. Off. . |
| 0434035 | 6/1991 | European Pat. Off. . |
| 0519512 | 12/1992 | European Pat. Off. . |
| 0558022 | 9/1993 | European Pat. Off. . |
| 664754 | 2/1988 | Switzerland . |

OTHER PUBLICATIONS

Weiner et al., Journal of Pharmacology and Experimental Therapeutics, 180(2):411–434, (1972).
ATCC Catalogue of Bacteria & Bacteriophages, 18th Ed., (1992), p. 22.
Chemical Abstracts, Ensign, C., et al., vol. 61, No. 2, (Jul. 20, 1964), No. 2208f.
Database WPI, AN92–409786, abstract of Japanese Published Patent Application No. 4304893 (Oct. 28, 1993).
Chemical Abstracts, Nagasawa, I., (Mar. 28, 1994), No. 120:161783u.
Chemical Abstracts, Hughs, D. E., vol. 47, No. (Mar. 25, 1953), No. 2832h.
Chemical Abstracts, Foks, H. et al., vol. 66, No. 21, (May 22, 1967), No. 94996s.
Chemical Abstracts, Yamamoto, T. et al., vol. 107, No. 25, (Dec. 21, 1987), No. 228395w.
Setcliff et al., J. of Chem. and Eng. Data, (1976), vol. 21, No. 2, p. 246.

*Primary Examiner*—Herbert J. Lilling
*Attorney, Agent, or Firm*—Fisher, Christen & Sabol

[57] ABSTRACT

The microbiological process for the production of hydroxy-heterocyclic carboxylic acid of formula

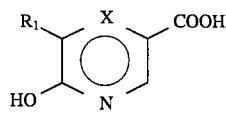

I wherein $R_1$ means a hydrogen or a halogen atom and X means a nitrogen atom or a $CR_2$ function, wherein $R_2$ means a hydrogen or halogen atom, starting from the corresponding heterocyclic carboxylic acid. The process is performed so that an aerobic biomass which utilizes nicotinic acid, is cultivated in a molar ratio of nicotinic acid to mineral acid of 1 to 8. The ratio is assured over the entire cultivation phase. The the hydroxylation of the corresponding heterocyclic carboxylic acid of the general formula

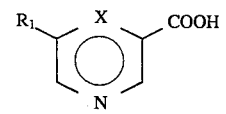

II wherein $R_1$ and X have the above-mentioned meanings, is performed with the biomass. Under these conditions, strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202 are concentrated in the cultivation phase.

16 Claims, No Drawings

5,516,661

MICROBIOLOGICAL PROCESS FOR THE PRODUCTION OF AROMATIC HYDROXY-HETEROCYCLIC CARBOXYLIC ACIDS

This application is a Continuation of prior U.S. application Ser. No. 07/984,450 filed Dec. 2, 1992 which is now abandoned.

BACKGROUND OF THE INVENTION

1. Field of the Invention

The invention relates to a new microbiological process for the production of hydroxy-heterocyclic carboxylic acids of the general formula:

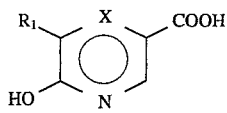

wherein $R_1$ means a hydrogen or a halogen atom and X means a nitrogen atom or a $CR_2$ function, wherein $R_2$ means a hydrogen or halogen atom, by means of an aerobic biomass which utilizes nicotinic acid or its soluble salts, which starts from the corresponding heterocyclic carboxylic acid or its soluble salt.

2. Background Art

In the following, the phrase "nicotinic acid" is meant to also include its soluble salts, especially its water soluble salts, such as, sodium nicotinate as alkali salt of nicotinic acid.

These hydroxy-heterocyclic carboxylic acids are important intermediate products for the production of pharmaceutical agents. For example, 6-hydroxynicotinic acid is an important intermediate product for the production of 5,6-dichloronicotinic acid (Swiss Patent No. 664,754), which in turn represents an initial product for pharmaceutical active ingredients.

A known embodiment for a microbiological process for the hydroxylation of nicotinic acid to 6-hydroxynicotinic acid is described, for example, in European Published Patent Application No. 152,948. This process is structured so that at first microorganisms are cultivated with nicotinic acid in the presence of yeast extract and then, for the actual biotransformation, the concentration of nicotinic acid as the feedstock is selected so that the catabolism of the nicotinic acid is inhibited on the first step of the 6-hydroxynicotinic acid. This process has the drawback that the cultivation of microorganisms using nicotinic acid takes place in the presence of yeast extract with which the cell-free fermentation solution is, contaminated after the cultivation or biotransformation, which leads to a contamination of the isolated 6-hydroxynicotinic acid. Another drawback lies in that this process is performed with homogeneous (biologically pure) cultures of microorganisms that are especially susceptible to infections in large-scale fermentations.

BROAD DESCRIPTION OF THE INVENTION

The main object of the invention is to eliminate the above-mentioned drawbacks (and the drawbacks mentioned below regarding U.S. Ser. No. 07/894,009 and European Patent Application No. 92-110425.3) and to provide a simple and ecological microbiological process for the production of hydroxy-heterocyclic carboxylic acids according to formula I. Other objects and advantages of the invention are set out herein or are obvious herefrom to one skilled in the art.

The objects and advantages of the invention are achieved by the processes and microorganisms of the invention.

The invention involves a microbiological process for the production of hydroxy-heterocyclic carboxylic acids of the general formula:

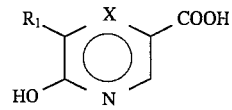

wherein $R_1$ is a hydrogen or a halogen atom and X is a nitrogen atom or a $CR_2$ function, wherein $R_2$ is a hydrogen or halogen atom. In the process, in step (a), an aerobic biomass which utilizes nicotinic acid or its soluble salts is cultivated with nicotinic acid or its soluble salts and a mineral acid in a molar ratio of nicotinic acid or its soluble salts to the mineral acid of 1 to 8. This ratio is maintained over the entire cultivation phase. Then, in step (b), the hydroxylation of the corresponding heterocyclic carboxylic acid of the general formula:

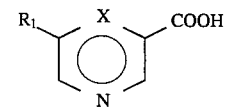

wherein $R_1$ and X have the above-mentioned meanings, or its soluble salts, is performed with the biomass. Preferably, in step (a), sulfuric acid in a molar ratio of nicotinic acid or its soluble salts to sulfuric acid of 3 to 5 is used as the mineral acid. Preferably, in the cultivation phase in step (a), microorganisms of strain *Pseudomonas acidovorans* DSM 7205, and/or strain *Pseudomonas acidovorans* DSM 7203, and/or strain *Alcaligenes faecalis* DSM 7204 and/or strain *Arthrobacter crystallopoietes* DSM 7202 are concentrated and then, in step (b), the hydroxylation takes place with these microorganisms. Preferably, in step (b) as the heterocyclic carboxylic acid, nicotinic acid or its soluble salts is hydroxylated to 6-hydroxynicotinic acid. Preferably, in step (b) as the heterocyclic carboxylic acid, pyrazine carboxylic acid or its soluble salts is hydroxylated to 5-hydroxypyrazine carboxylic acid. Preferably the cultivation in step (a) and the hydroxylation in step (b) are performed at a temperature of 15° to 50° C. and a pH of 5 to 9.

The invention also includes the microorganisms which utilize nicotinic acid or one of its soluble salts, of the strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202.

The invention further includes the process for the production of 6-hydroxynicotinic acid by the hydroxylation of nicotinic acid, wherein the hydroxylation is performed by microorganisms which utilize nicotinic acid or one of its soluble salts, of the strain *Pseudomonas acidovorans* DSM 7205, and/or strain *Pseudomonas acidovorans* DSM 7203, and/or strain *Alcaligenes faecalis* DSM 7204 and/or strain *Arthrobacter crystallopoietes* DSM 7202.

From commonly-owned U.S. Ser. No. 07/894,009 (filed on Jun. 4, 1992), which corresponds to European Patent Application No. 02-110425.3, a microbiological process for the production of 5-hydroxypyrizine carboxylic acid starting from pyrazine carboxylic acid is known. In such process homogeneous (biologicaly pure) cultures of microorganisms are cultivates for the actual hydroxylation with an alkali salt of the nicotinic acid. Accordingly, such process also has the drawback that it is performed with homogeneous cultures of microorganisms that are especially susceptible to infections in large-scale fermentations.

DETAILED DESCRIPTION OF THE INVENTION

According to the invention the process is carried out in that (a) an aerobic biomass which utilizes nicotinic acid is cultivated with nicotinic acid and a mineral acid in a molar ratio of nicotinic acid to mineral acid of 1 to 8, and the ratio is assured over the entire cultivation phase, and then (b) the hydroxylation of the corresponding heterocyclic-carboxylic acid of the general formula:

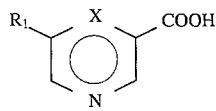

wherein $R_1$ and X have the above-mentioned meanings, or its soluble salts, is performed with the biomass to the desired hydroxylated end product according to formula I.

By the phrase "cultivating aerobic biomass which utilizes nicotinic acid or its salts", the following is meant: if biomass is cultivated, for example, from sewage sludge as an inoculum with the described molar nicotinic acid-mineral salt ratio under aerobic conditions, an aerobic biomass which utilizes nicotinic acid is obtained, i.e., a biomass that grows with nicotinic acid as the sole (only) carbon, nitrogen and energy source in the presence of oxygen. As inoculum soil, samples from various countries can also be used, such as, soil from the city park in Stanander (Spain) or soil from the vineyard in Visperterminen near Visp (Switzerland).

In contrast to the already-described (prior art) processes, the process according to the invention is performed not with homogeneous (biologically pure) cultures of microorganisms, but it is performed with a biomass consisting of mixed cultures.

The molar ratio of nicotinic acid to the mineral acid, i.e., the addition of the mixture consisting of nicotinic acid and mineral acid to the cell suspension, takes place so that a molar ratio of nicotinic acid to mineral acid of 1:1 to 8:1 is maintained during the entire cultivation phase. Mineral acids, such as, sulfuric acid, hydrochloric acid, nitric acid or phosphoric acid can be used, Preferably, sulfuric acid is used. Suitably the addition of the mixture takes place during the cultivation of the biomass so that a molar ratio of nicotinic acid to sulfuric acid of 3 to 5 is assured. That is, suitably 3 to 5 mol of nicotinic acid per mol of sulfuric acid is used for the cultivation. Preferably, 4 to 5 mol of nicotinic acid per mol of sulfuric acid is used for the cultivation.

Usually the cultivation of the aerobic biomass, which utilizes nicotinic acid, takes place in a mineral salt medium, preferably in the mineral salt medium whose composition is described in Table 1. The cultivation of the biomass takes place suitably at a pH of 5 to 9, preferably at pH 6 to 8. Suitably the temperature during the cultivation of the biomass is between 15° and 50° C., preferably between 25° and 40° C. Usually the cultivation of the biomass takes place over a period of 0.5 to 3 days.

Suitably, under these conditions microorganisms of strain *Pseudomonas acidovorans* DSM 7205, or strain *Pseudomonas acidovorans* DSM 7203, or strain *Alcaligenes faecalis* DSM 7204 or strain *Arthrobacter crystallopoietes* DSM 7202, or their mixtures, are concentrated in the cultivation phase.

The microorganisms DSM 7205, DSM 7203, DSM 7204 and DSM 7202 were deposited on Aug. 13, 1992 in the Deutsche Sammlung von Mikroorganismen und Zellkulturen GmbH, Mascheroderweg 1b, D-3300 Braunschweig, Germany, according to the Budapest Treaty. These microorganisms are not yet known from the literature and accordingly are also a component of the invention. It was not yet possible to identify the microorganism with the designation DSM 7202 taxonomically nor to assign it to a genus.

The taxonomy of microorganisms *Pseudomonas acidovorans* DSM 7205, i Pseudomonas acidovorans DSM 7203, and *Alcaligenes faecalis* DSM 7204 is described below.

The taxonomic description of *Pseudomonas acidovorans* DSM 7205 is:

| Properties of the strain: | |
| --- | --- |
| cell shape | rods |
| width, micron | 0.8–0.9 |
| length, micron | 1.5–9.0 |
| mobility | + |
| flagella | polar 1 |
| gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.7 | − |
| MacConkey's broth | + |
| SS agar | + |
| Cetrimide agar | + |
| testosterone | − |
| pigments | |
| nondiffusing | − |
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| glucose | − |
| fructose | + |
| xylose | − |
| adonite | − |
| L-arabinose | − |
| cellobiose | − |
| dulcitol | − |
| glycerol | + |
| m-inositol | − |
| lactose | − |
| maltose | − |
| raffinose | − |
| L-rhamnose | − |
| salicin | − |
| D-sorbitol | − |
| saccharose | − |
| trehalose | − |
| ethanol | + |
| dulcitol | − |
| ONPG/PNPG | − |
| ADH | − |
| VP | − |
| indole | − |
| $NO_2$ from $NO_3$ | + |
| phenylalanine desaminase | w |
| levan from saccharose | − |
| lecithinase | − |
| urease | − |
| hydrolysis of | |
| starch | − |
| gelatin | − |
| casein | w |

| Properties of the strain: | |
|---|---|
| DNA | − |
| Tween 80 | + |
| aesculin | − |
| PHB | − |
| tyrosine catabolism | + |
| use of substrate | |
| acetate | + |
| adipate | + |
| caprate | + |
| citrate | + |
| glycolate | + |
| laevulinate | + |
| malate | + |
| malonate | + |
| phenyl acetate | + |
| L-arabinose | − |
| fructose | + |
| glucose | − |
| mannose | − |
| maltose | − |
| D-xylose | − |
| mannitol | + |
| gluconate | + |
| 2-ketogluconate | + |
| N-acetylglucosamine | − |
| L-serine | − |
| quinate | + |
| D,L-tryptophan | + |
| L-tartrate | + |
| acetamide | + |
| α-aminobutyrate | + |
| ethanol | w |

The taxonomic description of *Pesudomonas acidovorans* DSM 7203 is:

| Properties of the strain: | |
|---|---|
| cell shape | rods |
| width, micron | 0.8–1.0 |
| length, micron | 2.6–6.0 |
| mobility | + |
| flagella | polar 1 |
| gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.7 | − |
| MacConkey's broth | + |
| SS agar | + |
| Cetrimide agar | + |
| testosterone | − |
| pigments | |
| nondiffusing | − |
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| glucose | − |
| fructose | + |
| xylose | − |
| adonite | − |
| L-arabinose | − |
| cellobiose | − |
| dulcitol | − |
| glycerol | + |
| m-inositol | + |
| lactose | − |
| maltose | − |
| raffinose | − |
| L-rhamnose | − |
| salicin | − |
| D-sorbitol | − |
| saccharose | − |
| trehalose | − |
| ethanol | −? |
| dulcitol | − |
| ONPG/PNPG | − |
| ADH | − |
| VP | − |
| indole | − |
| $NO_2$ from $NO_3$ | + |
| phenylalanine desaminase | w |
| levan from saccharose | − |
| lecithinase | − |
| urease | − |
| hydrolysis of | |
| starch | − |
| gelatin | − |
| casein | + |
| DNA | − |
| Tween 80 | + |
| aesculin | − |
| PHB | − |
| tyrosine catabolism | + |
| use of substrate | |
| acetate | + |
| adipate | + |
| caprate | + |
| citrate | + |
| glycolate | + |
| laevulinate | + |
| malate | + |
| malonate | + |
| phenyl acetate | + |
| L-arabinose | − |
| fructose | + |
| glucose | − |
| mannose | − |
| maltose | − |
| D-xylose | − |
| mannitol | + |
| gluconate | + |
| 2-ketogluconate | + |
| N-acetylglucosamine | − |
| L-serine | − |
| quinate | + |
| D,L-tryptophan | + |
| L-tartrate | + |
| acetamide | + |
| α-aminobutyrate | w |
| ethanol | + |

The taxonomic description Alcaligenes faecalis DSM 7204 is:

| Properties of the strain: | |
|---|---|
| cell shape | rods |
| width, micron | 0.6–0.8 |
| length, micron | 1.0–2.0 |
| mobility | + |
| flagella | peritrichous |
| gram reaction | − |
| lysis by 3% KOH | + |

-continued

| Properties of the strain: | |
|---|---|
| aminopeptidase (Cerny) | + |
| oxidase | + |
| catalase | + |
| growth | |
| anaerobic | − |
| 37°/41° C. | +/+ |
| pH 5.7 | − |
| MacConkey's broth | + |
| SS agar | + |
| Cetrimide agar | + |
| pigments | |
| nondiffusing | − |
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| D-glucose | − |
| D-fructose | + |
| D-xylose | − |
| ONPG/PNPG | − |
| ADH | − |
| VP | − |
| indole | − |
| $NO_2$ from $NO_3$ | + |
| denitrification | − |
| phenylalanine desaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine catabolism | + |
| use of substrate | |
| acetate | + |
| adipate | − |
| caprate | + |
| citrate | + |
| glycolate | + |
| laevulinate | − |
| D-malate | + |
| malonate | + |
| phenyl acetate | + |
| L-arabinose | − |
| D-fructose | − |
| D-glucose | − |
| D-mannose | − |
| maltose | − |
| D-xylose | − |
| mannitol | − |
| gluconate | − |
| 2-ketogluconate | + |
| N-acetylglucosamine | − |
| L-serine | − |

In the following, the phrase "heterocyclic carboxylic acid (substrate) to be hydroxylated" is meant to also include its salts, such as, its water soluble alkaline salts.

After the cultivation, the biomass can then be separated for the actual biotransformation (hydroxylation) either in a way usual to one skilled in the art or by directly adding the heterocyclic carboxylic acid (general formula II) to be hydroxylated to the cultivated biomass.

The actual hydroxylation of the heterocyclic carboxylic acid (substrate) takes place in a way known to one skilled in the art with nongrowing cells. Preferably, the actual hydroxylation of the heterocyclic carboxylic acid takes place with the microorganisms concentrated in the cultivation phase of the strain *Pseudomonas acidovorans* DSM 7205, strain *Pseudomonas acidovorans* DSM 7203, strain *Alcaligenes faecalis* DSM 7204 or strain *Arthrobacter crystallopoietes* DSM 7202, or with mixtures of these.

As the substrate, for example, nicotinic acid, pyrazine carboxylic acid or their halogenated derivatives can be used. As the halogenated derivatives of nicotinic acid or pyrazine carboxylic acid, for example, 5-chloronicotinic acid, 4-chloronicotinic acid or 6-chloropyrazine carboxylic acid can be used. Preferably nicotinic acid is hydroxylated to 6-hydroxynicotinic acid or pyrazine carboxylic acid is hydroxylated to 5-hydroxypyrazine carboxylic acid. The substrate for the biotransformation can be added continuously or batchwise. Suitably the substrate addition takes place so that the substrate amount in the fermenter does not exceed 20 percent by weight, preferably 15 percent by weight.

As medium for the hydroxylation those usual to one skilled in art can be used, preferably either the mineral salt medium described in Table 1 or the A-N medium described in Table 4. Usually the biotransformation is performed with cells that have an optical density at 550 nm ($OD_{550}$) or at 650 nm ($OD_{650}$) of 5 to 100. Suitably the biotransformation is performed at a pH of 5 to 9, preferably of 6.5 to 7.5 and at a suitable temperature of 15° to 50° C., preferably of 25° to 35° C.

After a usual reaction time of 5 to 24 hours the hydroxylated heterocyclic carboxylic acid, according to general formula I, can be isolated by methods usual to one skilled in the art, e.g., by acidification of the cell-free fermentation solution or by precipitation in the form of poorly soluble salts. Preferably as the hydroxylated heterocyclic carboxylic acid, 6-hydroxynicotinic acid or 5-hydroxypyrazine carboxylic acid is isolated.

EXAMPLE 1

(a) Cultivation of the biomass

The fermentation was performed in an unsterile mineral salt medium (Table 1) with 1 g of nicotinic acid per liter, in a fermenter with a working volume of 15 l at pH 7.0, at a temperature of 30° C. and an aeration rate between 5 to 20 l/min. For pH regulation, only acid in the form of an aqueous suspension consisting of 307 g of nicotinic acid (2.5 mol) and 49 g (0.5 mol) of $H_2SO_4$ and 1 l water from a vessel with a stirrer, which was fastened to the cover of the fermenter by a pneumatically controlled ball valve, was added to the medium. The fermenter was inoculated with 500 ml of sewage sludge from the waste water purification plant, in Visp, Switzerland (Table 2). After 36 hours the fermenter was emptied except for one liter and filled with fresh medium. This procedure was repeated after another 24 hours, 48 hours and 72 hours.

(b) Hydroxylation (production of 6-hydroxynicotinic acid)

When the optical density at 550 nm had reached a value between 5 to 20, the biomass was used to spectrophotometrically measure the specific 6-hydroxynicotinic acid formation rate. For this purpose, first the biomass was washed once with 0.9 percent (w/v) of NaCl solution. Then 10 µl of this cell suspension was added to a quartz cuvette (1 cm light path) preheated to 30° C., that contained 2990 μl of a solution consisting of 6.5 g of nicotinic acid/l, 10.1 g of $K_2HPO_4$/l and 4.0 g of $KH_2PO_4$/l, pH 7.0. The absorption of the cuvette at 550 nm was measured and then, from the same vessel, the linear increase of the absorption at 295 nm per minute was calculated. The specific activity (U) was determined according to the formula below:

$$U = \frac{A_{295nm} \cdot 60}{OD_{550nm} \cdot \min}$$

The fermentations were repeated with a sludge sample from the Zermatt (Switzerland) sewage treatment plant, soil samples from Visperterminen, Switzerland, and soil samples from Lac de Joux, Switzerland and a soil sample from Santander, Spain (Table 2).

EXAMPLE 2

Production of 5-hydroxypyrazine carboxylic acid

The biomass from fermentations 4, 5 and 6 (Table 2) were centrifuged off and washed once in 0.9 percent (w/v) NaCl solution. Then the cells were resuspended in a liter of solution containing 0.5 mol (70 g) of pyrazine carboxylic acid ammonia salt, pH 7.0. The optical density at 650 nm was then 20. After an incubation time of 16 hours under aerobic conditions at pH 7.0 and a temperature of 30° C., a quantitative conversion from pyrazine carboxylic acid to 5-hydroxypyrazine carboxylic acid could be determined by UV spectroscopy. The formed 5hydroxypyrazine carboxylic acid was not catabolized from the microorganisms.

As a control test *Pseudomonas acidovorans* D3 (DSM 4746), which is especially suitable for the industrial production of 5-hydroxypyrazine carboxylic acid cultured as described above, was used for the reaction according to the process described in European Patent Application No. 92-110425.3 or corresponding U.S. Ser. No. 07/894,009. The results are summarized in Table 2.

TABLE 1

| Composition of the mineral salt medium | |
|---|---|
| $MgCl_2.6H_2O$ | 0.8 g/l |
| $CaCl_2$ | 0.16 g/l |
| $Na_2SO_4$ | 0.25 g/l |
| $K_3PO_4.2H_2O$ | 0.7 g/l |
| $Na_3PO_4.12H_2O$ | 2.4 g/l |
| SLF | 1.0 ml/l |
| FeEDTA | 15.0 ml/l |
| Composition of the trace elements (SLF) in the mineral salt medium: | |
| KOH | 15.0 g/l |
| $EDTANa_2.2H_2O$ | 100.0 g/l |
| $ZnSO_4.7H_2O$ | 9.0 g/l |
| $MnCl_2.4H_2O$ | 4.0 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| Composition of FeEDTA: | |
| EDTA $Na_2.2H_2O$ | 5.0 g/l |
| $FeSO_4.7H_2O$ | 2.0 g/l |
| (The pH of the solution was adjusted to 7.0) | |

TABLE 2

| | Inoculum | $OD_{550}$ before activity measurement | Special activity $(A_{295} \cdot OD_{550}^{-1})$ | |
|---|---|---|---|---|
| (1) | ARA LONZA | 5.3 | 35.5 | |
| (2) | Lac de Joux | 14 | 20 | |
| (3) | ARA Zermatt | 9.6 | 26 | |
| (4) | Vineyard V'terminen | 12 | 44 | |
| (5) | soil Spain | 10 | 32 | |
| (6) | control *Pseudomonas acidovorans* | 3.5<br>8 | 35.1<br>39 | double determination |

Note:
Places where the microorganisms were found:
(1) Sewage sludge from the sewage treatment plant of the LONZA company in Visp, Switzerland.
(2) Soil from the banks of Lac de Joux, Le Sentier, Switzerland.
(3) Sewage sludge from the sewage treatment plant in Zermatt, Switzerland.
(4) Soil from the vineyard in Visperterminen in Visp, Switzerland.
(5) Soil from the city park in Santander, Spain

EXAMPLES 3 to 6

From the cultivated biomass according to Example 1 (a), the following microorganisms were able to be concentrated:

*Pseudomonas acidovorans* DSM 7205

*Pseudomonas acidovorans* DSM 7203

*Alcaligenes faecalis* DSM 7204

*Arthrobacter crystallopoietes* DSM 7202

These microorganisms were cultivated under the following conditions and used for the hydroxylation of nicotinic acid from 6-hydroxynicotinic acid. The results are summarized in Table 3.

In this connection the microorganisms were cultivated in a 7 l fermenter containing 5 l of A-N medium (Table 4) with 2 g of sodium nicotinate per 1 at a temperature of 30° C. and a pH of 7.0. For pH regulation, 5 N NaOH and 8.5 percent (v/v) $H_3PO_4$ were used. After 18 hours of growth, an additional 2 g of sodium nicotinate per 1 was added to the fermentation solution. As soon as the cells were in the exponential growth phase, the fermentation was interrupted and the microorganisms separated from the medium by centrifugation. Then the cells were resuspended in 500 ml of a solution containing 0.27 mol (40 g) of sodium nicotinate, pH 7.0. The optical density was then 20. The hydroxylation of nicotinic acid to 6-hydroxynicotinic acid was tracked spectrophotometrically (Table 3).

TABLE 3

| Examples | Time necessary for the hydroxylation of 0.27 mol nicotinic acid in 500 ml | Isolated amount of 6-hydroxynicotinic acid after acidification of the cell-free solution | Yield in % relative to nicotinic acid |
|---|---|---|---|
| Example 3: DSM 7202 | 22 hours | 15.7 g (0.11 mol) | 41 |
| Example 4: DSM 7203 | 9 hours | 30.1 g (0.22 mol) | 80 |
| Example 5: DSM 7204 | 10 hours | 28.1 g (0.2 mol) | 73 |
| Example 6: | 5 hours | 32.0 g (0.23 mol) | 85 |

TABLE 3-continued

| Examples | Time necessary for the hydroxylation of 0.27 mol nicotinic acid in 500 ml | Isolated amount of 6-hydroxynicotinic acid after acidification of the cell-free solution | Yield in % relative to nicotinic acid |
|---|---|---|---|
| DSM 7205 | | | |

TABLE 4

| A + N medium | |
|---|---|
| Composition | Concentration (mg/l) |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamine hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | $5 \cdot 10^{-3}$ |
| $FeSO_4.7H_2O$ | $2 \cdot 10^{-3}$ |
| (pH of the solution was adjusted to 7.0) | |

What is claimed is:

1. A process for the production of a hydroxy-heterocyclic carboxylic acid of formula:

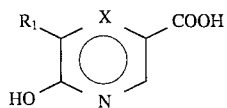

wherein $R_1$ is a hydrogen or a halogen atom and X is a nitrogen atom or a $CR_2$ function, wherein $R_2$ is a hydrogen or a halogen atom, consisting of:

(a) cultivating an aerobic biomass which has microorganisms which utilize nicotinic acid or one of its soluble salts, with nicotinic acid or one of its soluble salts and a mineral acid in a molar ratio of nicotinic acid or one of its soluble salts to the mineral acid of 1:1 to 8:1, said molar ratio being maintained over the entire cultivation phase, the aerobic biomass consisting of at least one strain of microorganisms selected from the group consisting of strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202, the cultivation of said aerobic biomass increasing said microorganisms in number and providing a cultivated biomass;

(b) contacting the corresponding heterocyclic carboxylic acid of formula:

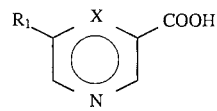

wherein $R_1$ and X have the above-mentioned meanings, or one of its soluble salts, with said cultivated biomass, and hydroxylating said heterocyclic carboxylic acid of formula I by means of said cultivated biomass; and (c) isolating the hydroxy-heterocyclic carboxylic acid of formula I.

2. A biologically pure culture of a microorganism which utilizes nicotinic acid or one of its soluble salts, selected from the group consisting of strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202, said biologically pure culture of said microorganism being obtained by cultivating an aerobic biomass containing said microorganism with nicotinic acid or one of its soluble salts and a mineral acid in a molar ratio of nicotinic acid or one of its soluble salts to the mineral acid of 1:1 to 8:1, to provide a cultivated aerobic mass containing said microorganism, and isolating said microorganism from said microorganism from said cultured aerobic mass to provide said biologically pure culture of said microorganism.

3. A process for the production of a hydroxy-heterocyclic carboxylic acid of formula:

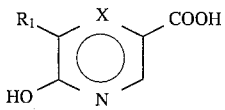

wherein $R_1$ is a hydrogen or a halogen atom and X is a nitrogen atom or a $CR_2$ function, wherein $R_2$ is a hydrogen or halogen atom, consisting of:

(a) cultivating a biomass which has microorganisms which utilize nicotinic acid or one of its soluble salts, under aerobic conditions with nicotinic acid or one of its soluble salts and a mineral acid in a molar ratio of nicotinic acid or one of its soluble salts to the mineral acid of 1:1 to 8:1, to provide a cultivated biomass having said microorganisms increased in number, said molar ratio being maintained over the entire cultivation phase, the cultivated biomass consisting of at least one strain of microorganisms selected from the group consisting of strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202;

(b) contacting the corresponding heterocyclic carboxylic acid of formula:

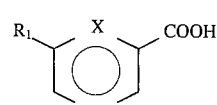

wherein $R_1$ and X have the above-mentioned meanings, or one of its soluble salts, with said cultivated biomass, and hydroxylating said heterocyclic carboxylic acid of formula I by means of said cultivated biomass; and (c) isolating the hydroxy-heterocyclic carboxylic acid of formula I.

4. A process for the production of 6-hydroxynicotinic acid by hydroxylation of nicotinic acid, comprising hydroxylating nicotinic acid by means of at least one strain of microorganisms which utilize nicotinic acid or one of its salts, selected from the group consisting of strain *Pseudomonas acidovorans* DSM 7205, strain *Pseudomonas acidovorans* DSM 7203, strain *Alcaligenes faecalis* DSM 7204 and strain *Arthrobacter crystallopoietes* DSM 7202, and mixtures thereof, a mineral acid being present at the start of the hydroxylation in an amount so that there is a molar ratio of the nicotinic acid to the mineral acid of 1:1 and 8:1.

5. The process according to claim 1 wherein, in step (a) sulfuric acid in a molar ratio of nicotinic acid or one of its soluble salts to the sulfuric acid of 3:1 to 5:1 is used as the mineral acid.

6. The process according to claim 5 wherein, in step (b) as the heterocyclic carboxylic acid, nicotinic acid or one of its soluble salts is hydroxylated to 6-hydroxynicotinic acid.

7. The process according to claim 5 wherein, in step (b) as the heterocyclic carboxylic acid, pyrazine carboxylic acid or one of its soluble salts is hydroxylated to 5-hydroxypyrazine carboxylic acid.

8. The process according to claim 7 wherein the cultivation in step (a) and the hydroxylation in step (b) are performed at a temperature of 15° to 50° C. and a pH of 5 to 9.

9. The process according to claim 1 wherein, in step (b) as the heterocyclic carboxylic acid, nicotinic acid or one of its soluble salts is hydroxylated to 6-hydroxynicotinic acid.

10. The process according to claim 1 wherein, in step (b) as the heterocyclic carboxylic acid, pyrazine carboxylic acid or one of its soluble salts is hydroxylated to 5-hydroxypyrazine carboxylic acid.

11. The process according to claim 1 wherein the cultivation in step (a) and the hydroxylation in step (b) are performed at a temperature of 15° to 50° C. and a pH of 5 to 9.

12. The process of claim 1 wherein the mineral acid is selected from the group consisting of sulfuric acid, hydrochloric acid, nitric acid and phosphoric acid.

13. The microorganism of claim 2 which is strain *Pseudomonas acidovorans* DSM 7205.

14. The microorganism of claim 2 which is strain *Pseudomonas acidovorans* DSM 7203.

15. The microorganism of claim 2 which is strain *Alcaligenes faecalis* DSM 7204.

16. The microorganism of claim 2 which is strain *Arthrobacter crystallopoietes* DSM 7202.

* * * * *